US012658298B1

(12) United States Patent
Emmons et al.

(10) Patent No.: US 12,658,298 B1
(45) Date of Patent: Jun. 16, 2026

(54) REDUCING LATENCY IN MEDICATION RECONCILIATION AFTER HOSPITAL DISCHARGE

(71) Applicant: WALGREEN CO., Deerfield, IL (US)

(72) Inventors: Stacey Emmons, Lexington, KY (US); Alexandra Broadus, Lake Bluff, IL (US)

(73) Assignee: WALGREEN CO., Deerfield, IL (US)

( * ) Notice: Subject to any disclaimer, the term of this patent is extended or adjusted under 35 U.S.C. 154(b) by 1062 days.

(21) Appl. No.: 16/991,437

(22) Filed: Aug. 12, 2020

(51) Int. Cl.
| | |
|---|---|
| *G16H 20/10* | (2018.01) |
| *G06N 20/00* | (2019.01) |
| *G16H 10/60* | (2018.01) |
| *G16H 80/00* | (2018.01) |

(52) U.S. Cl.
CPC ............. *G16H 20/10* (2018.01); *G06N 20/00* (2019.01); *G16H 10/60* (2018.01); *G16H 80/00* (2018.01)

(58) Field of Classification Search
CPC ........ G16H 20/10; G16H 10/60; G16H 80/00; G06N 20/00
See application file for complete search history.

(56) References Cited

PUBLICATIONS

Li, Q., Spooner, S.A., Kaiser, M. et al. An end-to-end hybrid algorithm for automated medication discrepancy detection. BMC Med Inform Decis Mak 15, 37 (2015). https://doi.org/10.1186/s12911-015-0160-8 (Year: 2015).*
Tang, Y., Yang, J., San Ang, P., Dorajoo, S. R., Foo, B., Soh, S., . . . & Tung, A. (2019). Detecting adverse drug reactions in discharge summaries of electronic medical records using Readpeer. International journal of medical informatics, 128, 62-70. (Year: 2019).*
National Committee for Quality Assurance (NCQA), "Medication Reconciliation Post-Discharge (MRP)". Retrieved from the Internet at: <URL:https://www.ncqa.org/hedis/measures/medication-reconciliation-post-discharge/> accessed on Jul. 28, 2020 (2020), 2 pages.

* cited by examiner

*Primary Examiner* — Karlheinz R. Skowronek
*Assistant Examiner* — Nidhi Dharithreesan
(74) *Attorney, Agent, or Firm* — MARSHALL, GERSTEIN & BORUN LLP; Randall G. Rueth

(57) ABSTRACT

Techniques for discovering or predicting that a patient is eligible for a post-hospital discharge medication reconciliation process are disclosed. The prediction is based on automatically applying a machine learning model to one or more incoming prescription orders, where the model has been generated from statistically analyzing a plurality of historical prescriptions to determine prescription attributes and/or values thereof that are more strongly correlated to hospital discharges than are other prescription attributes and/or values. When a prescription order is discovered to be associated with a hospital discharge, the named patient is deemed eligible for medication reconciliation, and an alert is generated so that pharmacy personnel may initiate a post-hospital discharge medication reconciliation process for the patient. As such, patient health outcomes may be improved after being discharged from the hospital, as post-hospital discharge medication reconciliations are able to be completed within 30 days of the patient's discharge using the disclosed techniques.

20 Claims, 4 Drawing Sheets

300

HOSPITAL — 345

MTM SYSTEM — 350

LOCAL COMPUTING SYSTEM — 302

305 — PROCESSOR(S)

308 — MEMORIES

312 — HOSPITAL DISCHARGE PREDICTOR

310 — ML MODEL

315 — USER INTERFACE(S)

318 — COMMUNICATION INTERFACE(S)

320

322

HEALTH CARE PROVIDER(S) — 352

HEALTH PLAN PROVIDER — 348

SERVER(S) — 325

PROCESSOR(S) — 328

MEMORIES — 330

HOSPITAL DISCHARGE PREDICTOR — 332

ML MODEL — 335

ML MODEL TRAINER — 340

COMMUNICATION INTERFACE(S) — 338

TRAINING DATA — 342

400

REDUCING LATENCY IN MEDICATION RECONCILIATION AFTER HOSPITAL DISCHARGE

TECHNICAL FIELD

The present invention relates generally to systems and methods for decreasing latency in post-hospital discharge medication reconciliation processes.

BACKGROUND

Medication reconciliation is an important safety issue for patients who have been discharged from hospital. A medication reconciliation process compares a patient's hospital discharge medication orders to the medications which had been prescribed to the patient prior to the patient entering into the hospital with the aim of reconciling any dangers and/or discrepancies in pharmaceutical treatment of the patient after hospital discharge. Generally speaking, a medication reconciliation process is directed to preventing medication errors and/or other issues related to medications which may compromise and/or endanger the patient's recovery and health. A medication reconciliation process typically includes building a complete list of a patient's medications (including both pre-hospital admittance and post-hospital discharge prescriptions, over-the-counter drugs, vitamins, etc.), as well as obtaining information on the patient's medication compliance, health and allergy history, etc., verifying the medications and other information for accuracy, reconciling the list of medications, and documenting any changes. A pharmacist or a certified pharmacy technician typically performs the medication reconciliation process, including consulting with the patient and optionally other medical providers to build the list, address any drug interactions, omissions, duplications, inconsistencies, and resolve the need to or to not continue and/or modify any medications and/or therapies. Medication discrepancies and/or errors can negatively affect patient outcomes, thus completing a medication reconciliation process as soon as possible following the patient being discharged from the hospital is advantageous and important.

Generally, a pharmacist or certified pharmacy technician must complete a medication reconciliation process for a patient within 30 days of the patient being discharged from the hospital. FIG. 1 shows a typical information flow pathway of a medication reconciliation process 100 that is currently practiced, from a point in time at which a hospital 102 discharges a patient 104 (e.g., at "DAY 0," as indicated by reference 106) to a health plan provider 108 (e.g., an insurance provider, a coordination of care provider, etc.) of the patient 104 receiving a notification 109 that a post hospital discharge medication reconciliation process 100 for the patient 104 has been completed. Specifically, upon the patient 104 being discharged 106 from the hospital 102, the hospital 102 sends a file 110 of the discharged patient to the patient's health plan provider 108. Based on the received patient file 110, the health plan provider 108 identifies that the patient 104 has been discharged from the hospital 102 and, as such, provides at least a portion of the patient file and optionally other information 112 to a third-party provider 114, e.g., a Medication Therapy Management (MTM) vendor 114, to initiate a post hospital discharge medication reconciliation process 100 for the patient 104. The MTM vendor 114 aggregates information from the received patient file 112, the patient's discharge medication list, a pre-hospitalization medication list of the patient, and optionally other patient information, and forwards at least portions of the aggregated patient file 116 to the patient's pharmacy 118. (In an alternate branch within the information flow 100, the health plan provider 108 may send the patient file directly to the pharmacy 118, as denoted by reference 120.) Either way (e.g., via references 112 and 116, or via reference 120), the pharmacy 118 is alerted 122 to the need for performing a medication reconciliation process 100 for the patient 104 due to the patient 104 being discharged 106 from the hospital 102. Accordingly, the pharmacy 118 initiates a medication reconciliation intervention or consultation 124 with the patient 104 or with an agent of the patient, e.g., when the patient 104 or the patient's agent picks up a medication prescription for the patient 104 at the pharmacy 118 or at another time. Upon the completion of the medication reconciliation intervention or consultation 124 and optionally other steps of the medication reconciliation process 100, the pharmacy 118 reports the medication reconciliation service outcome 128 to the MTM vendor 114. The MTM vendor 114 then notifies 109 the health plan provider 108 (and optionally other parties, such as the patient's health care provider) that the post-hospital discharge medication reconciliation process 100 for the patient 104 has been completed.

Within the currently-practiced information flow pathway 100, though, one of the most significant barriers to pharmacies completing medication reconciliation processes within the 30-day window after patients have been discharged from hospitals is data latency of the health plan provider 108 and/or of the third party MTM vendor 114. That is, the completion of the process 100 within 30 days of the patient's hospital discharge 106 depends on timely processing and delivery of, for example, the patient file 112 by the health plan provider 108 to the MTM vendor 114, followed by timely processing and delivery of the patient file 116 by the MTM vendor 114 to the pharmacy 118 so that the pharmacy 118 is notified 122 of the need to initiate a post-hospital discharge medication reconciliation consultation 124 (and other subsequent actions) with the patient with sufficient time to complete the medication reconciliation process before 30 days post-discharge. Typically, delays at the insurance/health plan provider 108 and/or the MTM vendor 114 result in the pharmacy 118 not being notified 122 of the need for a medication reconciliation process for the patient 104 with sufficient remaining time. For instance, as shown in the example scenario of FIG. 1, the pharmacy 118 does not even get notified 122 of the need for a medication reconciliation process 100 for the patient 104 until after the 30 days post-discharge have passed. Unfortunately, these delays are common occurrences, and may result in increased risk to the recovery and health of the patient 104. Indeed, recent data collected by a pharmacy enterprise indicates that around 40% of patients who were discharged from the hospital and eligible for medication reconciliation did not have a medication reconciliation process completed within 30 days of their discharge date.

Given the limited time window in which a medication reconciliation process must be completed after a patient has been discharged from a hospital, a solution to decrease data latency and increase the speed by which this important process can be completed is needed.

SUMMARY

The present embodiments relate to systems, methods, and techniques for decreasing latency in reconciling medications of a patient after the patient has been discharged from a hospital. Additional, fewer, or alternative features described herein below may be included in some embodiments.

In an embodiment, a computer-implemented method includes receiving, by one or more processors associated with a pharmacy enterprise, a prescription order that is to be filled for a particular patient. The method also includes predicting that the prescription order is associated with a hospital discharge of the particular patient, including providing one or more attributes and/or attribute values of the prescription order as input to a machine learning model that has been generated based on performing one or more statistical analyses on historical prescription data to determine one or more prescription attributes and/or one or more prescription attribute values that are more strongly correlated to hospital discharges than are other prescription attributes and/or prescription attribute values. Additionally, the method includes generating an alert indicating that the particular patient is eligible for medication reconciliation based on an output of the machine learning model, where the output generated based on the one or more attributes and/or attribute values of the prescription order provided as the input. For example, the output may be indicative of a probability or a likelihood that the received prescription order is associated with a hospital discharge of the patient.

In an embodiment, a system associated with a pharmacy enterprise includes one or more processors; a communication interface; and one or more memories storing a machine learning model that has been generated from performing one or more statistical analyses on historical prescription data to determine one or more prescription attributes and/or prescription attribute values that are more strongly correlated to hospital discharges than are other prescription attributes and/or other prescription attribute values. The system further includes computer-executable instructions that are stored on the one or more memories and that, when executed by the one or more processors, cause the system to: receive, via the communication interface or via a user interface, a prescription order that is to be filled for a particular patient; predict that the prescription order is associated with a hospital discharge of the particular patient by providing one or more attributes and/or one or more attribute values of the prescription order as input to the machine learning model; and generate, based on the prediction, an alert indicating that the particular patient is eligible for medication reconciliation.

BRIEF DESCRIPTION OF THE DRAWINGS

Advantages will become more apparent to those skilled in the art from the following description of the embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

The figures described below depict various aspects of the applications, methods, systems, and techniques disclosed herein. It should be understood that each figure depicts an embodiment of a particular aspect of the disclosed applications, systems, methods, and techniques, and that each of the figures is intended to accord with one or more possible embodiments thereof. Furthermore, wherever possible, the following description refers to the reference numerals included in the following figures, in which features depicted in multiple Figures are designated with consistent reference numerals.

The figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

Figure 1:
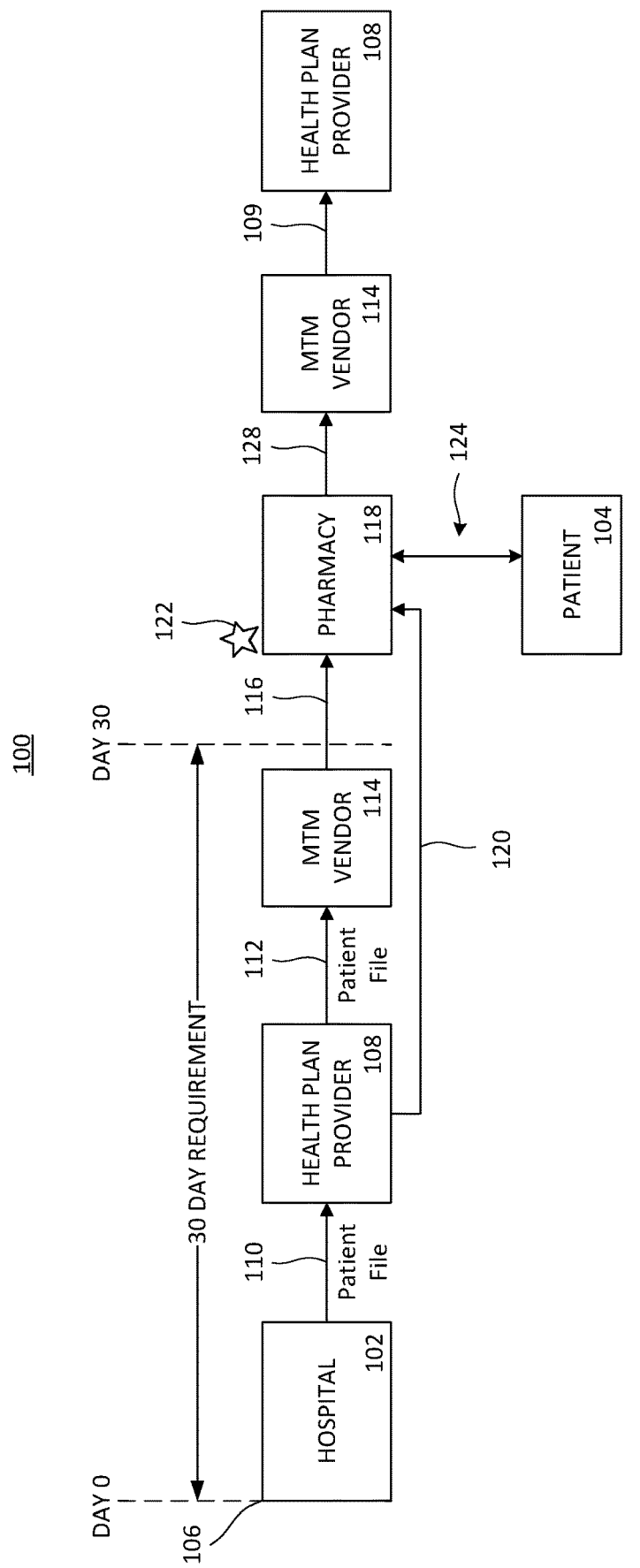
FIG. 1 illustrates a typical information flow pathway of a post-hospital discharge medication reconciliation process.

The systems, methods, and techniques disclosed herein generally relate to reducing the latency of medication reconciliation for a patient after the patient has been discharged from the hospital, e.g., so that the medication reconciliation process for the patient may be completed within 30 days of the patient's hospital discharge. In particular, instead of a pharmacy relying on a health plan provider or a medication therapy management (MTM) provider to initially notify the pharmacy that a medication reconciliation process for a patient needs to be performed, e.g., as denoted by reference 122 of FIG. 1, the systems, methods, and techniques disclosed herein allow the pharmacy to utilize a machine learning model to predict whether or not a received prescription order for a patient (e.g., any prescription order received by the pharmacy) is a hospital post-discharge medication order and, if so, initiate the medication reconciliation process for the named patient, e.g., with a patient medication reconciliation consultation or intervention.

In an embodiment, a pharmacy may receive a prescription (also interchangeably referred to herein as a "prescription order") that is to be filled for a patient. Upon the receipt of the prescription order, a computer system of the pharmacy may employ a machine learning model to predict, based on attributes and/or attribute values of the received prescription order, the likelihood or probability that the prescription is a hospital post-discharge medication order, that is, the likelihood or probability that the prescription order was issued in conjunction with the patient being discharged from a hospital. The machine learning model may have been trained or generated by analyzing historical prescription data to determine the attributes of prescription orders and the attributes' respective values that are more associated with patient hospital discharges than are other prescription attributes and/or attribute values, such as by using techniques described in this disclosure. For the received prescription, when the likelihood exceeds a certain threshold, the pharmacy computer system generates an alert indicating that the particular patient is eligible for a post-hospital discharge medication reconciliation. The alert may be presented in real-time at a user interface (e.g., when the prescription order for the patient is provided to the pharmacy), and/or the alert may be stored in an electronic file of the patient at the pharmacy computing system and presented to a pharmacy associate upon the pharmacy associate accessing the patient's file. Accordingly, when the patient (or an agent of the patient) interacts with a pharmacy associate to drop off and/or pick up the filled prescription, or otherwise interacts with a pharmacy associate for prescription and/or pharmacy purposes, the pharmacy associate, upon accessing the patient's file, may be alerted that the patient has been identified as eligible for a post-hospital discharge medication reconciliation, and as such may offer to initiate the medication reconciliation process for the patient, e.g., by performing or scheduling a consultation. The patient may agree to perform the medication reconciliation consultation immediately on-site, or may schedule a telephone or on-line consultation for a later date prior to 30 days after the patient's hospital discharge. As prescription orders for a patient who is being discharged from a hospital are typically sent to the patient's pharmacy either directly (e.g., electronically) from the hospital upon the patient's discharge, or manually within a few days of the patient's hospital discharge, by using the techniques described herein, the pharmacy is notified of the need for a post-hospital discharge medication reconciliation process much earlier in the 30 day window as compared to currently performed processes.

The systems, methods, and techniques of the present disclosure offer numerous advantages and benefits. For example, the disclosed systems, methods, and techniques allow a pharmacy to be notified of the need to perform a medication reconciliation process for a patient who has been discharged from the hospital as soon as a prescription order for the patient (which may have been prescribed upon the patient's hospital discharge) is received electronically or is otherwise entered into the pharmacy's computer system. As such, any data latency incurred by a health plan provider and/or by a third party (e.g., MTM vendor) is significantly decreased or even eliminated. Further, in some situations, conventional processes may result in the pharmacy being notified of the need for a medication reconciliation for a patient after the patient has already picked up a hospital discharge-related prescription, thus requiring the post-discharge patient to potentially make several needless trips to the pharmacy. Indeed, in some situations, conventional processes may result in the pharmacy being notified of the need for a medication reconciliation for a patient after the 30 day window has elapsed. On the other hand, the systems, methods, and techniques of the present disclosure may allow for the completion of a medication reconciliation process for every patient who has been discharged from the hospital within the required 30 day window, as the majority of patients fill post-hospital discharge prescription orders well within 30 days of their hospital discharge date, at which point the pharmacy is able to automatically discover (and therefore is notified of) the patients' respective hospital discharges. Thus, the disclosed systems, methods, and techniques may greatly improve post-hospital discharge medication reconciliation processes and technology. Significantly, the disclosed systems, methods, and techniques may increase compliance with the requirement to complete the medication reconciliation process for patients within 30 days of hospital discharge and, importantly, may contribute to patients' overall recovery, safety, health outcomes, and well-being.

Moreover, the systems and methods of the present disclosure do not merely automate manual tasks using a computer or computing system. Rather, the systems and methods automatically process prescription attributes in ways that a human does not and cannot do. For example, pharmacy associates (e.g., humans) do not include a trained model via which the pharmacy associates evaluate prescription attributes of incoming prescriptions to predict which of the incoming prescriptions are likely to be hospital post-discharge medication orders. Indeed, given the volume and rate at which prescription orders from various sources are received by certain pharmacies, it would be impossible for a human to assess each incoming prescription accurately and quickly enough to ascertain those that are associated with hospital discharge and complete their required medication reconciliation processes within the 30 day windows, let alone with probabilistic confidence. Moreover, embodiments of the present techniques include utilizing a machine learning model that has been trained on historical prescription data, which is not a mental act of a human.

Figure 2:
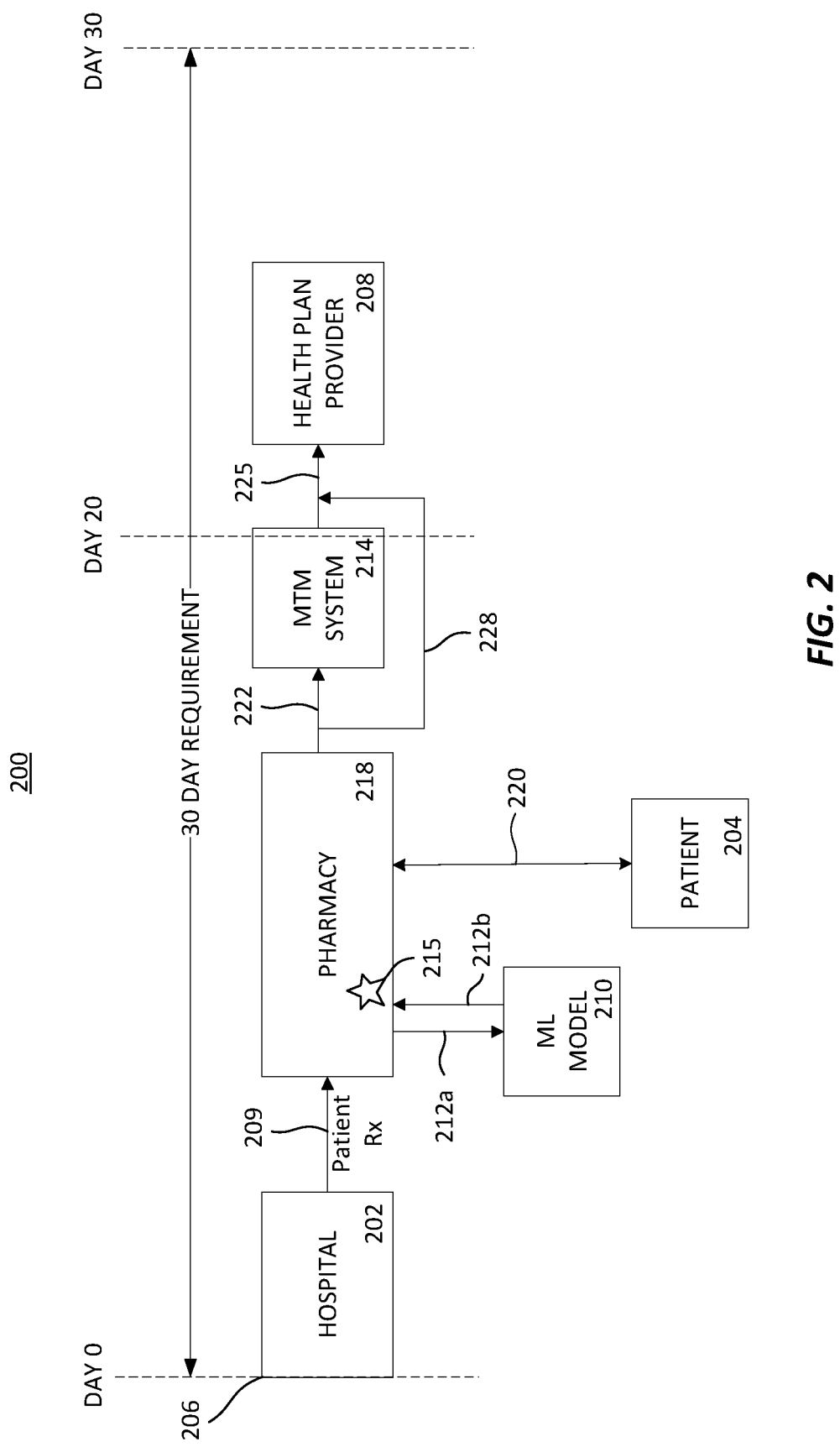
FIG. 2 illustrates an example information flow pathway of a post-hospital discharge medication reconciliation process in accordance with the principles and techniques described in this disclosure.

Turning now to FIG. 2, FIG. 2 illustrates an example information flow pathway 200 of a medication reconciliation process in accordance with embodiments of the systems, methods, and techniques of the present disclosure. In particular, FIG. 2 illustrates the information flow pathway 200 from a point in time at which a hospital 202 discharges a patient 204 (e.g., at "DAY 0," as indicated by reference 206), to the health plan provider 208 of the patient 204 being notified 225 that a post-hospital discharge medication reconciliation process for the patient 204 has been completed. As shown in FIG. 2, a pharmacy 218 receives a prescription order 209 that is to be filled for a patient 204 (e.g., an incoming prescription order), where, unbeknownst to the pharmacy 218, the order 209 was prescribed in conjunction with the discharge 206 of the patient 204 from the hospital 202. The prescription 209 may have been electronically transmitted from the hospital 202 directly to a computing system of the pharmacy 218, as depicted by reference 209 in FIG. 2. Alternately, the prescription 209 may have been electronically transmitted from a health care provider of the patient other than the hospital 202 (not shown in FIG. 2), or the prescription 209 may have been delivered or presented (e.g., via paper, via electronic format on a patient's personal computing device, or via any other suitable format) to the pharmacy 218 by the patient 204 or by an agent of the patient 204 (also not shown in FIG. 2). An agent of the patient may be, for example, a parent, guardian, caregiver, or other proxy of the patient who is authorized to manage (e.g., present, pickup, etc.) prescriptions on behalf of the patient. Generally speaking, the prescription 209 may have been written or otherwise authorized by a prescriber associated with the hospital such as a physician, a clinician, or other healthcare staff, and the prescription 209 is typically related to the patient's hospital stay and/or post-discharge care. Additionally, the pharmacy 218 may be a particular physical or virtual location of a plurality of pharmacy locations that are owned, operated, and/or administered by a pharmacy enterprise, in embodiments. For example, the pharmacy 218 may be a local pharmacy retail store front, a satellite pharmacy branch located in a hospital or other facility, a mail-order prescription fulfillment center, a website or on-line prescription fulfillment system, a mobile application, etc.

Typically, the pharmacy 218 does not have a priori knowledge that the received prescription order 209 is associated with a hospital discharge. Accordingly, the received prescription order 209 is entered into and stored in a computing system of the pharmacy, and the pharmacy computing system automatically determines a likelihood or probability that the received prescription 209 is associated with a hospital discharge of the patient for whom the prescription is written, e.g., is a post-hospital discharge prescription. That is, the pharmacy computing system processes incoming prescription orders to automatically discover or determine which of the incoming prescription orders (if any) corresponds to a hospital discharge of the named patient.

In the embodiment illustrated in FIG. 2, a machine learning (ML) model 210 that is stored at the pharmacy computing system analyzes or otherwise operates on one or more attributes and/or attribute values of the received prescription order 209 (as denoted by references 212a, 212b) to determine the likelihood or probability of the received prescription order 209 being a post-hospital discharge prescription order, e.g., a prescription that was prescribed upon, in conjunction with, or due to the discharge of the patient 204 from a hospital. The model 210 may be at least partially deployed or executed, for example, on one or more computing devices of the pharmacy computing system that are locally disposed at the location of the pharmacy 218 at which the prescription was received, and/or the model 210 may be at least partially deployed or executed at one or more back-end servers of the pharmacy computing system. The application of the model 210 to the one or more attributes and/or attribute values of the received prescription order 209 (as denoted by references 212a, 212b) may be triggered by any stage during the processing and/or filling of the prescription by the pharmacy 218, for example, when the pharmacy 218 initially receives or acknowledges the reception of the prescription, when the pharmacy 218 initiates, completes, or performs any intermediate stage of the processing or filling of the prescription, or at any stage of processing the prescription, so long as the model 210 is accessed and operates 212a, 212b on the prescription attributes/attribute values prior to the filled prescription being picked up by the patient or the patient's agent.

The model 210 may include one or more trained machine learning models, deep learning models, neural networks, trained artificial intelligence models, and/or other suitable models, for example. Accordingly, the model 210 may be generated based on one or more statistical analyses of historical data of prescription orders (which include both prescription orders issued in conjunction with hospital discharges as well as other prescription orders) to determine, discover, or identity one or more attributes of prescription orders and/or specific values of those attributes that are more likely to be associated (e.g., more strongly correlated, either alone or in combination) with hospital discharges than are other attributes of prescription orders. That is, as the model 210 is trained to determine the likelihood or probability of prescription orders being associated with hospital discharges, "hospital discharge" may be an independent variable of the model 210, and dependent variables of the model 210 may include the one or more attributes of prescriptions and/or values of prescription attributes that are more likely to be associated with hospital discharges than are other attributes and/or attribute values of prescriptions. Example prescription attributes and/or attribute values which may possibly be determined to be more strongly correlated to hospital discharges for a given set of training data may include, but are not limited to: medication type, name, and/or dosage, combinations or groups of medications, facility name and/or location, prescriber NPI, prescriber's group name, condition for which prescription is a therapeutic, etc. In some embodiments, the model 210 is trained to also determine the respective strengths of impact of prescription attributes and/or prescription attribute values on the correlation(s), and in these embodiments the selection or identification of particular attributes/attribute values as dependent variables of the model 210 may be based on the strengths of impact, for example.

The contributing attributes and/or attribute values (e.g., the dependent variables of the model 210) and their respective strengths of impact may be determined based on, for example, one or more predetermined thresholds, similarity values, confidence levels, and/or any other type of suitable metric and/or combinations thereof. In an example, regression analysis, clustering, supervised learning, semi-supervised learning, unsupervised learning, reinforcement learning, and/or any other suitable training technique may be performed on the historical prescription data to discover or learn a subset of prescription attributes and/or prescription attribute values that are more strongly correlated to hospital discharges than are other prescription attributes and/or prescription attribute values, and optionally their respective weights (e.g., strengths of impacts, association, correlation, etc.) with respect to hospital discharge. As such, the model 210 may be generated based on the discovered subset of prescription attributes and/or prescription attribute values, and optionally based on the respective weights of the discovered prescription attributes/attribute values. The training and development of the model 210 is discussed in greater detail elsewhere within this disclosure.

Returning to the information flow 200, one or more attributes and/or attribute values of the prescription order 209 are extracted or otherwise obtained by the pharmacy computing system, and the obtained prescription attributes and/or prescription attribute values are provided as input 212a to the model 210. The one or more prescription attributes/attribute values provided as input 212a may be a selected subset or an entirety of the attributes/attribute values of the prescription 209, for example. Examples of prescription attributes include attributes which are indicative of:

- patient name, address, weight, age, and/or other demographic information;
- prescriber name, address, NPI (National Provider Identifier) number, and/or DEA (Drug Enforcement Administration) number;
- hospital name, address, and/or NPI;
- facility name, address, and/or NPI;
- one or more medication name, type, strength, concentration, amount, mode, dosage, directions, and/or course of therapy;
- date of order; and
- therapeutic purpose of order. Of course, this set of examples is non-limiting, and other types of prescription attributes are additionally or alternately possible.

Generally speaking, as utilized herein, the term "prescription attribute" is utilized interchangeably with the term "prescription parameter," and a "value" of a prescription attribute or prescription parameter is utilized to indicate particular content of the prescription attribute or parameter. For example, for an example prescription order, a specific prescription parameter may be "hospital name," and the value of the prescription parameter "hospital name" on the particular prescription order may be "Lutheran General Hospital." The prescription attributes and/or or prescription attribute values may be extracted and/or obtained by the pharmacy computing system by using any suitable technique, e.g., electronically as delineated within an electronic prescription order, by image processing, by database retrieval, by data entry, by electronic code scanning or processing, etc.

The model 210 operates on the one or more prescription attributes and/or prescription attribute values 212a and determines, as an output 212*b*, a likelihood that the prescription order 209 is associated with a discharge of the patient 204 from a hospital, and therefore that the patient 204 is eligible for post-hospital discharge medication reconciliation. When the likelihood exceeds a pre-determined threshold, confidence level, or other suitable metric, the patient 204 is identified 215 to the pharmacy 218 as being eligible for a post-hospital discharge medication reconciliation process. That is, based on the output of the model 210, the pharmacy 218 is notified 215 that a post-hospital discharge medication reconciliation process is needed for the patient 204. For example, an alert indicative of the need to perform a post-hospital discharge medication reconciliation for the patient 204 may be presented on a display screen or user interface utilized by the pharmacy associate, and/or may be stored in conjunction with a file of the patient 204 which is stored at the pharmacy computing system. The alert may be a visual (textual or graphic) alert displayed on user interface of the pharmacy computing system, or an audio, or a haptic alert transmitted to any suitable device operated by the pharmacy associate. Additionally or alternatively, the alert may be implemented as a printed message on a label of prescribed medication(s), or on the instructions for medication(s). In some embodiments, the pharmacy computing system may push an alert to a patient's personal computing device and/or to a personal computing device of the patient's agent.

Although FIG. 2 depicts the use of an ML model 210 to determine whether or not an incoming prescription order is associated with a hospital discharge, in other embodiments, instead of using an ML model 210 to process or analyze attributes of the received prescription, a pharmacy computing system may determine the likelihood of the received prescription 209 being associated with a hospital discharge based on a set of pre-determined rules (not shown in FIG. 2), where the set of pre-determined rules are generated, for example, based on specific features/attributes or a combination of attributes and/or attribute values of prescription orders that have been determined (e.g., statistically determined) a priori to be more indicative of hospital discharges (e.g., as compared to other features/attributes of prescription orders). For instance, regression analysis, clustering, supervised learning, semi-supervised learning, unsupervised learning, reinforcement learning, and/or any other suitable training technique may be performed on historical prescription data to discover or learn a subset of prescription attributes and/or prescription attribute values that are more strongly correlated to and/or associated with hospital discharge than are other prescription attributes/prescription attribute values, and optionally the attributes' and/or attribute values' respective weights (e.g., strengths of impacts) with respect to hospital discharge. Examples of prescription attributes and/or attributes values which may be determined as being more correlated (either alone or in combination) to hospital discharges may include, but are not limited to: medication type, name, dosage, and/or type or category, combinations or groups of medications, facility name and location, prescriber NPI, prescriber's practice or group name, condition treated, etc. The discovered prescription attributes and/or prescription attribute values (and optionally their respective weights) may be indicated in a set of rules that are stored at the pharmacy computing system, e.g., locally and/or remotely at back-end server(s). Of course, the set of rules may be determined by additionally or alternatively utilizing techniques other than statistical analysis of historical prescription data. At any rate, the set of rules stored at the pharmacy computing system may be implemented using any suitable or desired format, e.g., as a decision tree, a table, etc.

At any rate, whether by using an ML model 210, a set of pre-determined rules, or some other suitable technique that is automatically applied to attributes of incoming prescription orders by the pharmacy computing system, based on a positive determination of the patient's need for a post-hospital discharge medication reconciliation, e.g., as indicated by the alert 215, a pharmacy associate may offer to initiate a post-hospital discharge medication reconciliation process for the patient 204. Upon the patient's acceptance of the offer, a pharmacy associate may consult with the patient (or the patient's agent) (reference 220) as one of multiple steps of the post-hospital discharge medication reconciliation process. The consultation may be offered and performed at any stage of the providing, filling, and/or picking up the prescription order, or any other desired time prior to the expiration of the 30 day window from hospital discharge 206. For example, when a patient inquires, at the pharmacy, about the status of her prescription, a pharmacy associate may access the patient's file, and based on the alert stored in the patient's file, the pharmacy associate may offer and/or initiate a post-hospital discharge medication reconciliation consultation 220 with the patient. In another example, the consultation may be offered prior to the patient arriving at the pharmacy, via, for example, an alert at the patient's personal computing device, where the alert was generated when an electronic prescription order was received from the hospital 202 and immediately processed by the pharmacy 218 by utilizing the ML model 210. In another example, the patient may be identified and alerted of the consultation offer, e.g., via her personal computing device or via any other suitable device when she enters the premises of the pharmacy. The patient 206 may agree to a post-hospital discharge medication reconciliation consultation 220, and the medication reconciliation consultation may occur, for example, on-site at the pharmacy 218 at prescription pickup, or on another date via a telephone, video call, or any other suitable remote communication means, etc., within the 30 day window of the patient 204 being discharged from the hospital (reference 206).

At any point after the pharmacy 218 discovers that an incoming prescription is associated with a hospital discharge 215 and the patient agrees to the corresponding post-hospital discharge medication reconciliation process (reference 220), the pharmacy 218 may request, retrieve, or otherwise obtain the patient's file and/or other related information (not shown in FIG. 2) from the hospital 202, the health plan provider 208 of the patient 204, one or more health care providers of the patient, and/or an MTM system 214. The patient's file and/or other related information may contain the patient's discharge medication list, the patient's pre-hospitalization medication list, the patient's health and allergy history, and/or other information. In some embodiments, the patient's file may be transmitted by the hospital 202 directly to the pharmacy 218 along with the prescription order 209. Additionally or alternatively, the pharmacy 218 may separately request that the file be delivered from the hospital 202, and/or dialogue or communicate with other parties and/or systems such as the patient's primary care physician, the attending hospital physician, the patient's health plan provider 208, prescription dispensing systems, etc. to obtain and/or reconcile any other information needed by the pharmacy 218 to complete the patient's post-hospital discharge medication reconciliation process.

Generally, a pharmacist or a qualified pharmacy technician may perform the medication reconciliation consultation 220 with the patient 204 or with the patient's agent, and may initiate and coordinate the other actions (e.g., communicating with and/or obtaining data from the hospital 202, health care providers, other pharmacies, third parties, etc.) that are needed to complete the post-hospital discharge medication reconciliation process for the patient 204. Additionally, the pharmacist or qualified pharmacy technician may generate and document the outcome of the medication reconciliation process of the patient 204. As medication reconciliation processes are generally aimed at discovering and addressing any medication discrepancies, errors, and other issues, an outcome of a post-hospital discharge medication reconciliation process for the patient 204 may include information indicative of the patient's reconciled course of pharmaceutical therapy/therapies, which may include changes to the patient's pre-hospitalization course of therapy/therapies and/or other changes.

The pharmacy 218 may provide the outcome of the completed post-hospital discharge medication reconciliation process to the MTM system 214 (reference 222). For example, the pharmacist or qualified pharmacy technician may generate and document (e.g., save or store) the outcome at a computing system associated with the MTM system 214, and/or the pharmacist or the qualified pharmacy technician may generate and document the outcome at the pharmacy computing system, and provide a copy thereof to the MTM system 214. The MTM system 214 may forward or provide information indicative of the completion of the patient's post-hospital medication reconciliation process to the patient's health plan provider 208 (reference 225), and optionally to other parties such as the patient's primary care provider and/or other health care provider(s) (not shown in FIG. 2). In an alternate path within the information flow 200, the pharmacy 218 may directly provide the outcome of the patient's post-hospital discharge medication reconciliation process to the patient's health plan provider 208, as denoted by reference 228. It is noted that in FIG. 2, the MTM system 214 may be external to the pharmacy 218, such as when the MTM system 214 is administered by a third-party vendor. In some implementations, though, the MTM system 214 may be owned, operated, and/or administered by the pharmacy enterprise of which the pharmacy location 218 is a part.

Accordingly, as demonstrated by the information flow 200, by using the techniques described here, the pharmacy 218 is able to discover (and therefore, self-notify itself of) a patient who is eligible for a post-hospital discharge medication reconciliation process 215 well before 30 days after the date of the patient's discharge 206. For example, when the hospital 202 (or a health care provider associated with the hospital 202) directly sends the patient's discharge-related prescription order 209 on the day of the patient's discharge 206, the pharmacy 218 may apply the model 210 to the prescription order 209 upon its receipt, thereby discovering that the patient 204 as a post-hospital discharge patient 215 (and therefore is in need of a post-hospital discharge medication reconciliation process) on the same day as the patient's discharge 206. In another example, when the patient 204 or the patient's agent manually provides the discharge-related prescription order to the pharmacy 218, the manual delivery of the discharge-related prescription order typically occurs within a week or a few days after the patient discharge 206, or, in some cases, on the same day as the patient's discharge 206, thereby identifying that the patient 204 as a post-discharge patient 215 and is in need of a post-hospital discharge medication reconciliation process within a week, a few days, or even the same day as the patient's discharge 206. At any rate, using embodiments of the systems, methods, and techniques disclosed within, the pharmacy 218 automatically and timely discovers 215 that a patient named on an incoming prescription order has been discharged from the hospital 202 and is in need of a post-hospital discharge medication reconciliation process for the patient 204 in sufficient time to complete the process prior to the 30 day deadline. In the example scenario shown in FIG. 2, the health plan provider 208 is notified of the completion of the patient's post-hospital discharge medication reconciliation process (reference 225) within 20 days of the patient's discharge 206. As such, by using embodiments of the systems, methods, and techniques disclosed herein, data latency incurred by the health plan provider 208 and/or third-party MTM vendors 214 in currently implemented post-hospital discharge medication reconciliation processes may be greatly reduced or even eliminated. Consequently, a greater percentage of discharged patients may be availed of post-hospital discharge medication reconciliation processes and their respective benefits and advantages.

It is noted that the systems, methods, and techniques disclosed herein are easily applied to multiple prescription orders which are issued upon a patient's hospital discharge. For example, the multiple prescription orders may be processed by the ML model 210 sequentially, and/or may be processed in parallel by multiple instances of the ML model 210 executing at the pharmacy computing system. In an embodiment, when any one of the multiple prescription orders is determined to be associated with a hospital discharge, a corresponding alert may be generated, e.g., in a manner such as described above.

Further, in embodiments, the pharmacy computing system 218 may apply the ML model 210 to every prescription order that the pharmacy 218 receives, whether electronically or manually from any source. That is, by applying the ML model 210 to every incoming prescription, the pharmacy is automatically able to discover and filter out post-hospital discharge prescriptions. As such, the pharmacy 218 may be notified of an even greater percentage of patients needing post-hospital discharge medication reconciliation processes, and consequently the health outcomes of an even greater number of patients may be improved.

Figure 3:
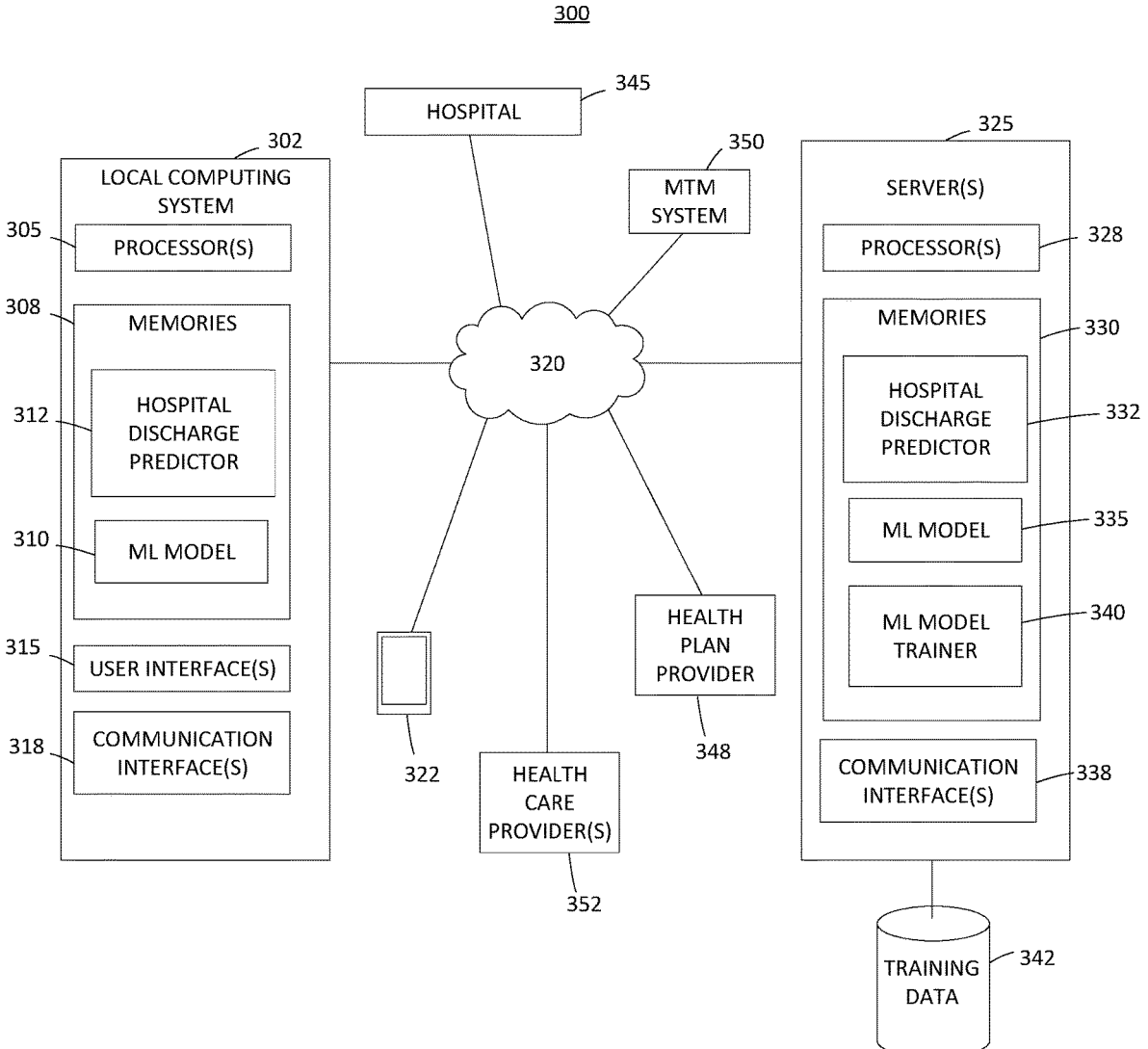
FIG. 3 is a simplified block diagram of an example system for discovering, identifying, and/or otherwise determining, based on incoming prescription orders, patients who have been discharged from the hospital and for whom medication reconciliations are needed.

FIG. 3 is a simplified block diagram of an example system 300 for discovering patients who have been discharged from a hospital and are in need of a medication reconciliation process based on incoming prescription orders. At least portions of the system 300 may be utilized, for example, in conjunction with the information flow 200 of FIG. 2. For example, at least portions of the system 300 may be implemented by and/or included in a computing system of the pharmacy 218. The system 300 is discussed with simultaneous reference to the information flow 200; however, this is for ease of illustration purposes only and is not limiting.

As shown in FIG. 3, the system 300 includes a local computing system 302 which may be disposed, for example, at a physical or virtual location associated with a pharmacy enterprise at which incoming prescriptions are received, such as at a local pharmacy retail storefront, a satellite pharmacy branch located in a hospital or other facility, a mail-order prescription fulfillment location, an Internet or web-based order prescription fulfillment location, a mobile application, etc. The local computing system 302 may include one or more processors 305 and one or more tangible, non-transitory memories, memory storage devices, or data storage units 308.

Each of the one or more processors 305 may be a programmable microprocessor that executes computer-executable instructions stored in the one or more memories 308 to execute some or all of the functions of the local pharmacy computing system 302 as described herein. Processor(s) 305 may include one or more central processing units (CPUs) and/or one or more graphics processing units (GPUs), for example. Alternatively, or in addition, some of the processors 305 may be other types of processors (e.g., application-specific integrated circuits (ASICs), field-programmable gate arrays (FPGAs), etc.), and some of the functionality of local computing system 302 as described herein may instead be implemented in hardware, in embodiments.

The one or more memories 308 may include one or more tangible, non-transitory memory storage devices or components, and may store thereon a machine learning (ML) model 310 which has been trained to determine a likelihood or a probability of a set of prescription attributes and/or prescription attribute values of an incoming prescription order being associated with a hospital discharge of the patient named on the prescription order, such an ML model similar to the model 210 of FIG. 2. In embodiments, the memories 308 may additionally or alternatively store one or more sets of pre-determined rules, such as those discussed with respect to FIG. 2.

Additionally, the memories 308 may store a hospital discharge predictor 312, which may comprise a set of computer-executable instructions that are executable by the one or more processors 305 to cause the local computing system 302 to discover or determine whether or not a patient named on an incoming prescription order has been discharged from a hospital (e.g., that the incoming prescription order is associated with a hospital discharge) and therefore is in need of a post-hospital discharge medication reconciliation process. For example, the local computing system 302 may receive an incoming prescription order via a user interface 315 of the local computing system 302 (e.g., a data entry screen, scanner, image processor, etc.), or the local computing system 302 may electronically receive an incoming prescription order via one or more wired and/or wireless communication interfaces 318, e.g., via one or more communication and/or data networks 320, e.g., from a hospital 345, a health care provider of the patient 352, etc. The one or more networks 320 may be a single communication and/or data network, or may include multiple communication and/or data networks (e.g., one or more wired and/or wireless local area networks (LANs), one or more wired and/or wireless wide area networks (WANs), which may include the Internet), one or more public and/or private networks, and/or one or more other types of networks. The incoming prescription order may be stored in the memories 308 of the local computing system 302, e.g., in conjunction with a file of the patient named on the order.

The hospital discharge predictor 312 may obtain prescription attributes and/or prescription values of the received prescription order using any suitable technique (such as data processing, image processing, data extraction, reading from a database, etc.) and may provide the obtained attributes/attribute values as input to the ML model 310. For example, the hospital discharge predictor 312 may obtain any prescription attributes and/or prescription attribute values that have been defined as inputs to the ML model 310, and/or the hospital discharge predictor 312 may input all prescription attributes and/or prescription attribute values into the ML model 310. The ML model 310 may operate on the input attributes and/or values (e.g., by utilizing respective weights of the inputs, etc.), and may generate an output indicative of a likelihood or probability that the incoming prescription order is associated with a hospital discharge. The hospital discharge predictor 312 may compare the output with one or more thresholds, confidence ranges or levels, and/or other suitable metrics to thereby discover or determine whether or not the incoming prescription order is associated with a hospital discharge. When the hospital discharge predictor 312 discovers or determines that an incoming prescription is indeed associated with a hospital discharge, the hospital discharge predictor 312 stores a corresponding indicator or alert in conjunction with the stored prescription order and/or the patient's file in the memories 308. In some embodiments, the hospital discharge predictor 312 may cause the alert or indication that the patient is in need of a post-hospital discharge medication reconciliation process to be displayed at one or more user interfaces (such as at a user interface of the local pharmacy computing system 302, and/or via the communication interface(s) 318 and network(s) at a user of a personal computing device of the patient or of an agent of the patient 322. The alert or indicator may be displayed at one or more of the user interfaces upon the hospital discharge predictor 312 discovering or determining that the incoming prescription is associated with a hospital discharge, when the patient's file is accessed by a pharmacy associate, etc.

Of course, in some implementations, the one or more memories 308 may store additional instructions and/or data utilized by the local computing system 302 (not shown in FIG. 3). For example, the one or more memories 308 may store a set of pre-determined rules (not shown) that are utilized by the local computing system 302 to process the incoming prescription's attributes/attribute values in lieu of the ML 310, such as in a manner described above with respect to FIG. 2.

In some arrangements of the system 300, the local computing system 302 of the local pharmacy location is communicatively coupled to one or more back-end servers 325 of the pharmacy enterprise, e.g., via the one or more communication and/or data networks 320. Generally speaking, the back-end server(s) 325 are located remotely from any of the local computing systems 302 of the system 300. The back-end server(s) 325 may include one or more processors 328 and one or more tangible, non-transitory memories, memory storage devices, or data storage units 330. In embodiments, the one or more back-end server(s) 325 may be implemented as a bank of servers, a virtual private network of computing devices, a cloud computing system, or any other suitable implementation.

In an example embodiment, the memories 330 of the back-end server(s) 325 store thereon master or approved versions of a hospital discharge predictor 332 and an ML model 335. In this example embodiment, the hospital discharge predictor 312 and ML model 310 which are stored at and executed by the local computing device 302 are instances of the master/approved hospital discharge predictor 332 and ML model 335, where the instances 312, 310 have been downloaded from the back-end server(s) 325 to the local computing system 302.

In an example embodiment, the back-end server(s) 325 process at least some of the incoming prescriptions of the local pharmacy computing system 302 and/or of other local pharmacy computing systems (not shown) of the system 300. For example, when an incoming prescription is received via a user interface 315 or a communication interface 318 of the local computing system 302, the local computing system 302 may forward the incoming prescription order and/or indications thereof to the back-end server(s) 325 for processing, e.g., via the network(s) 320 and one or more communication interfaces 338 of the server(s) 325. As such, the hospital discharge predictor 332 and the ML model 335 of the back-end server(s) 325 may operate on the incoming prescription and/or indications thereof in a manner similar to that discussed for the hospital discharge predictor 312 and ML model 310 of the local computing system 302. The hospital discharge predictor 332 may provide any resulting alerts and/or indications that patients need medication reconciliation processes performed to the local computing system 302, so that a pharmacist or certified pharmacy technician associated with the pharmacy location at which the local computing system 302 is disposed may initiate a consultation 220. Alternatively, a remote pharmacist or certified pharmacy technician who is associated with the pharmacy, but is not necessarily located at the particular location at which the local computing system 302 is disposed, may be provided with the alert/indication (e.g., via a respective user interface (not shown) that is communicatively connected to the server(s) 325 via the network(s) 320 and the communication interface(s) 338), and the remote pharmacist/pharmacy technician may accordingly initiate a medication reconciliation consultation with the patient or the patient's agent. Thus, in this example embodiment, the back-end server(s) 325 may provide or host an incoming prescription evaluation or screening service (e.g., via the hospital discharge predictor 332 and the ML model 335) to which the local computing system 302 (or any applications thereon) is exposed, or may otherwise access.

Generally speaking, though, any one or more portions of the incoming prescription evaluation or screening process may be performed locally by the local computing system 302 (e.g., by utilizing the hospital discharge predictor 312, the ML model 310, and/or other instructions stored on the memories 308); may be performed remotely by the back-end server(s) 325 (e.g., by utilizing the hospital discharge predictor 332, the ML model 335, and/or other instructions stored on the memories 330); or may be performed cooperatively by both the local computing system 302 and the back-end server(s) 325.

Further, as depicted in FIG. 3, the local computing system 302 and the back-end server(s) 325 may be communicatively connected, e.g., via the network(s) 320, to systems associated with the hospital 345 from which the patient was discharged, the health plan provider 348 of the patient, an MTM system 350, one or more health care providers 352 of the patient (which may include the prescriber of the prescription), etc. As such, the system 300 may easily obtain and/or request information from any of these parties 345, 348, 350, 352 that is needed to complete the post-hospital discharge medication reconciliation process for the patient. As previously discussed, in some configurations, the MTM system 350 may be owned, operated, and/or administered by a third-party vendor and/or associated with the health plan provider 348. In other configurations, the MTM system 350 may be owned, operated, and/or administered by the pharmacy enterprise and, in such configurations, the MTM system 350 may be implemented by the one or more back-end servers 325 and/or at the local computing system 302, for example (not shown in FIG. 3).

The memories 330 of the one or more server(s) 325 further store thereon an ML model trainer 340 which, in an embodiment, comprises a set of computer-executable instructions that are executable by the one or more processors 328 to generate and/or update the ML model 335, e.g., by performing one or more statistical analyses of training data 342 which includes data of a plurality of historical (e.g., actual) prescription orders, including respective prescription attributes and values thereof. The training data 342 includes both prescriptions associated with hospital discharges and prescriptions that are not associated with hospital discharges, and at least some of the prescriptions associated with hospital discharges are labeled or otherwise indicated as such. The ML model trainer 340 performs the statistical analyses to discover or otherwise determine a set of prescription attributes and/or prescription attribute values that are more strongly correlated to patient hospital discharge than are other prescription attributes and/or prescription attribute values. For example, the ML model trainer 340 may perform regression analysis, clustering, supervised learning, semi-supervised learning, unsupervised learning, reinforcement learning, and/or other types of statistical and/or learning techniques on the training data 342. Respective strengths of impact of prescription attributes and/or prescription attribute values may also be determined using the statistical analyses, and a subset of the prescription attributes and/or attribute values having the greatest strengths of impact (either individually or in combination) may be identified to be the inputs of the ML model 330.

The ML model trainer 340 may bound the total number and/or types of discovered input attributes and/or attribute values based on various data analyses criteria, such as individual and/or collective accuracies of the attributes and/or attribute values, a total number of discovered attributes and/or values, a size of training data set, and the like. Additionally or alternatively, the ML model trainer 340 may bound the total number and/or types of discovered input attributes and/or attribute values based on criteria associated with prescription orders (e.g., geographical location of issuance of order; geographical location of the filling of the order; medication type, name, dosage, regimen, and/or other medication characteristics; issuing facility name and/or location; prescriber NPI, group, and/or location; etc.). Still additionally or alternatively, the ML model trainer 340 may bound the total number and/or types of discovered input attributes and/or attribute values based on characteristics of patients, e.g., age, gender, other patient demographics, medical procedure, medical condition, type of surgery and/or other reason for hospital admittance, prescription fill history, pre-existing health conditions, allergies, etc. The bounding may be done a priori, e.g., by filtering the training data 342 based on desired bounding criteria prior to executing the statistical analyses, the bounding criteria may be accounted for by setting or otherwise using various criteria as independent variables (e.g., which prescription attributes and/or attribute values are most predictive of being associated with a hospital discharge for a given zip code, for a given medical condition, for a given type medication, etc.), the bounding may be performed a posteriori, e.g., by filtering or otherwise limiting the set of prescription attributes and/or attribute values that are to be utilized as inputs based on the boundary criteria, and the like. At least some bounding criteria may be determined a priori, or via user input during training, for example.

Accordingly, in some embodiments of the system 300, multiple different ML models 335 may be generated by the ML model trainer, each of which has been trained based on different boundary conditions or criteria. The multiple ML models 335 may be stored at the one or more servers 325, and a selected one or more of the multiple models 335 may be provided to the local computing system 302 to utilize as its locally stored model instances 310. In an example, at the local computing system 302, the hospital discharge predictor 312 may select one or more models from a plurality of locally stored ML models 310 to operate on some or all of the incoming prescriptions. Similarly, when the hospital discharge predictor 332 of the back-end server(s) 325 processes incoming prescriptions, the hospital discharge predictor 332 may utilize a selected one or more of the stored ML models 335 to process some or all of the incoming prescriptions.

As previously discussed, the trained ML model(s) 335 may be stored at the one or more servers 325, and/or may be provided by the one or more servers 325 to the local computing system 302 for use in processing incoming prescriptions. As such, in embodiments, incoming prescriptions that are received by the local computing system 302 (and that are by other local computing systems and the back-end server(s) 325, for that matter) may be added to the training data 342 as additional training data so that the set of training data 342 is updated. As such, one or more of the ML model(s) 335 may be updated by re-training the model(s) 335 using the updated set of training data. ML model training, re-training, and/or updating may occur periodically and/or on-demand, as desired, and trained ML models may be tested and validated (e.g., by using a set of testing or validation data, not shown), and adjusted prior to utilizing the ML models for live processing of incoming prescriptions at the local computing system 302 and/or the back-end server(s) 325.

Figure 4:
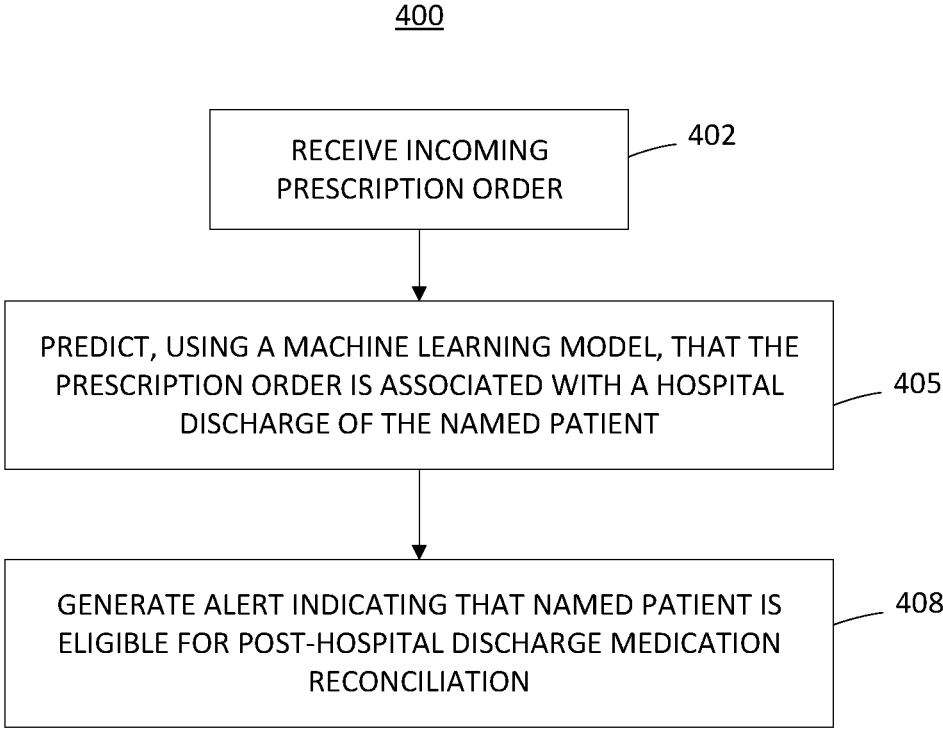
FIG. 4 is a flow diagram of an example method for discovering, identifying, and/or otherwise determining, based on incoming prescription orders, patients who have been discharged from the hospital and for whom medication reconciliations are needed.

FIG. 4 illustrates a flow diagram of an example method 400 for discovering or identifying patients who are eligible for medication reconciliations due to being discharged from a hospital based on prescription orders. In an embodiment, at least a portion of the method 400 may be performed by the system 300, or by other suitable systems. For example, at least portions of the method 400 may be performed by the local computing system 302 (e.g., by utilizing the hospital discharge predictor 312 and/or the ML model 310) and/or by the server(s) 325 (e.g., by utilizing the hospital discharge predictor 332 and/or the ML model 335). As such, embodiments of the method 400 may be computer-implemented and may be executed without any human input or interface. Further, in an embodiment, at least a portion of the method 400 may be performed in conjunction with the information flow 200. In embodiments, the method 400 may include additional or alternate steps other than those discussed herein. The method 400 is discussed with simultaneous reference to FIGS. 2 and 3, although this is for ease of illustration purposes only, and is not limiting.

At a block 402, the method 400 includes receiving, by one or more processors associated with a pharmacy enterprise, a prescription order that is to be filled for a particular patient, e.g., an incoming prescription order. The prescription order may be received electronically, e.g., via a communication interface, via database transfers and/or reads, via image processing, via scanning, etc., or the prescription order may be received manually via a user interface. The prescription order may be received at a local pharmacy computing system of the pharmacy enterprise, such as the local computing system 302, or the prescription order may be received at a back-end server system of the pharmacy enterprise, such as the back-end server(s) 325. The prescription order includes multiple prescription attributes or parameters, such as patient name, address, weight, age, and/or other demographic information; prescriber name, address, associated group, NPI number, DEA number, etc.; hospital or facility name and address; medication name, strength, type, dosage, regimen, directions, course of therapy, etc.; date order was issued; therapeutic purpose of order, such as condition to be treated; etc. The prescription attributes or parameters may have corresponding values which are particular to the prescription order. The received prescription order may be entered and stored in a local and/or back-end data storage entity of the pharmacy enterprise, such as may be stored in conjunction with a file of the patient named on the prescription order.

At a block 405, the method 400 includes predicting, by the one or more processors, that the prescription order is associated with a hospital discharge of the particular patient. For example, at the block 405, the method 400 may include providing one or more attributes and/or attribute values of the prescription order as input to a machine learning (ML) model, such as the ML model 210 or the ML model 335. The ML model typically has been generated or created based on performing one or more statistical analyses on historical prescription data to determine one or more prescription attributes and/or one or more prescription attribute values that are more strongly correlated to hospital discharges than are other prescription attributes and/or prescription attribute values, e.g., to determine the dependent variables of the ML model, such as in a manner described elsewhere herein. The historical prescription data based on which the ML model was generated and trained may include a plurality of historical prescription orders and respective indications of whether or not each historical prescription order was associated with a hospital discharge, e.g., was issued to the named patient upon the named patient's discharge from a hospital. For example, the ML model may have been trained by the ML model trainer 340 based on the training data 342, and subsequently validated, adjusted, tuned, etc. Any one or more attributes and/or attribute values of the received prescription order which correspond to the dependent variables of the ML model may be provided to the ML model as input, in an embodiment. For example, a medication name, dosage, regimen, and/or category of drug, an identification, practice or group name, and/or address or location of a prescriber, a name and/or an address of a facility, etc. of the received prescription order may be provided as input to the ML model. In some embodiments, an entirety of the attributes and/or attribute values of the received prescription order is provided to the ML model as input.

In some embodiments, at the block 405, other information may be provided as input to the ML model in conjunction with the attributes and/or attribute values of the received prescription. For example, information indicative of the patient and the patient's health history and/or conditions, such as patient demographics, prescription fill history, pre-existing and/or currently diagnosed conditions, allergies, other coinciding course(s) of treatment, etc. may be provided as input. In these embodiments, typically the ML model has been trained using both the historical prescription data and historical patient data, where the historical patient data includes various types of data associated with a plurality of patients and the patients' health histories and/or conditions, and least some of the historical patient data indicates whether or not respective patient data is associated with a hospital discharge. As such, the ML model has been trained to determine the attributes and/or attribute values associated with prescription orders and patients which are more likely (e.g., individually and/or in combination) than other prescription attributes and/or prescription attribute values to be indicative of a hospital discharge.

At any rate, the ML model may be applied to the inputs (in some cases, using respective weights of the inputs), and may generate an output indicative of a likelihood or probability that the received prescription order is associated with a hospital discharge of the patient named on the prescription order. As such, the block 405 may include obtaining the output which has been generated by the ML model based on the inputs corresponding to the received prescription, and comparing the output of the ML model to one or more thresholds, similarity values, confidence levels or ranges or any suitable metric of confidence or combination thereof. The confidence metrics may have been determined a priori, and may be adjustable. The received prescription order may be discovered, determined, or otherwise identified as being associated with the named patient's discharge from a hospital when the comparison of the output to the confidence metric(s) indicate that confidence in the output of ML model is sufficient (e.g., that the measure of likelihood or probability output by the ML model is above a confidence threshold). In some embodiments, the ML model itself performs the comparison of the likelihood or probability to the confidence metrics, and the ML model produces the indication of whether or not the received prescription order is associated with a discharge of the named patient from a hospital.

At a block 408, the method 400 includes generating, by the one or more processors, an alert indicating that the particular patient is eligible for medication reconciliation based on an output of the machine learning model, where the output has been generated based on the one or more attributes and/or attribute values of the prescription order provided as the input to the ML model. For example, the alert may be displayed or otherwise provided at a user interface of a local computing device, a remote computing device, or a handheld device utilized by a pharmacy associate, and/or the alert may be displayed or otherwise provided at a user interface of a computing device of the patient or an agent of the patient. The block 408 may include storing an indication of the alert in conjunction with a file of the patient at the pharmacy computing system, and presenting the alert (e.g., via a user interface) when the patient's file is accessed by pharmacy personnel.

As such, via the method 400, the pharmacy computing system may automatically discover, determine, or identify that a particular incoming prescription (e.g., of a plurality of incoming prescriptions) is associated with the named patient being discharged from a hospital, and consequently that the named patient is in need of or otherwise eligible for a post-hospital discharge medication reconciliation. Upon notification of pharmacy personnel, the patient, and/or the patient's agent, e.g., via the generated alert, the pharmacy personnel and the patient (or patient's agent) may schedule and/or perform a medication reconciliation consultation, thereby initiating the post-hospital discharge medication reconciliation process for the patient.

In some embodiments, the method 400 includes transmitting requests for information that is needed to complete the patient's post-hospital discharge medication reconciliation process (not shown). For example, the pharmacy computing system 302, 325 (e.g., under the guidance of a pharmacist, licensed pharmacy technician, or other pharmacy personnel who is working on and/or completing the patient's post-hospital discharge medication reconciliation process) may electronically transmit requests for such information to the discharging hospital, to one or more health care providers 352 of the patient (who may or may not be associated with the patient's hospital discharge), to the health plan provider 348 of the patient, to a third-party vendor 350 (e.g., an MTM vendor) associated with the health plan provider and/or with the pharmacy enterprise, etc., and respective responses to the requests may be electronically received from the same.

Additionally or alternatively, at least some of the respective responses may be manually received (e.g., via telephone or paper), and the responses may be entered into the pharmacy computing system 302, 325. Thus, the received responses may be utilized to complete the patient's post-hospital discharge medication reconciliation process.

In some embodiments, the method 400 includes providing an outcome of the completed post-hospital discharge medication reconciliation process of the patient to the patient's health plan provider 348 and/or to the third-party or MTM vendor 350. For example, the pharmacy computing system 302, 325 may transmit a file thereto including the outcome, or pharmacy personnel may enter the outcome directly into the receiving parties' systems. In some implementations, a copy or a summary of the outcome may be transmitted or otherwise provided to the patient, patient's agent, and/or one or more health care providers 352 of the patient. Generally, the outcome may include at least a reconciled medication list or list of courses of therapies of the patient post-hospital discharge, and a confirmation of any changes, deactivations, etc. of previously prescribed medications and/or therapies.

Therefore, the systems, methods, and techniques disclosed herein may reduce the latency of a medication reconciliation process for a patient after the patient has been discharged from the hospital, e.g., so that the patient's medication reconciliation process is able to be completed within 30 days of the patient's hospital discharge. Specifically, instead of a pharmacy enterprise needing to rely on a health plan provider or a medication therapy management (MTM) provider to initially notify the pharmacy enterprise that a medication reconciliation process for a patient needs to be performed due to hospital discharge, the systems, methods, and techniques disclosed herein allow the pharmacy enterprise to automatically discover or determine that an incoming prescription order for a patient is associated with a hospital discharge of the patient, and as such the pharmacy may immediately initiate a post-hospital discharge medication reconciliation process for the patient, thereby significantly reducing or even eliminating the latencies inherent in currently known processes and allowing the patient's medication reconciliation process to be completed within 30 days after the patient's hospital discharge date. Further, when the disclosed techniques are applied to every or even a majority of prescription orders that the pharmacy enterprise receives, the pharmacy enterprise is automatically able to discover and filter out post-hospital discharge prescription orders upon their respective receipts at the pharmacy computing system. As such, the pharmacy enterprise may be notified of an even greater percentage of patients in need of post-hospital discharge medication reconciliation processes with sufficient time to complete the processes within 30 days of discharge. Consequently, the health outcomes of an even greater number of patients may be improved.

Other Matters

Although the preceding text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based upon any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more modules of a computer system (e.g., a processor or a group of processors) may be configured by software (e.g., an application or application portion) as a module that operates to perform certain operations as described herein.

In various embodiments, a module (e.g., a hardware module) may be implemented mechanically or electronically. For example, a module may comprise dedicated circuitry or logic that is permanently configured (e.g., as a special-purpose processor, such as a field programmable gate array (FPGA) or an application-specific integrated circuit (ASIC) to perform certain operations. A module may also comprise programmable logic or circuitry (e.g., as encompassed within a general-purpose processor or other programmable processor) that is temporarily configured by software to perform certain operations. It will be appreciated that the decision to implement a module mechanically, in dedicated and permanently configured circuitry, or in temporarily configured circuitry (e.g., configured by software) may be driven by cost and time considerations.

Accordingly, the term "module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which modules are temporarily configured (e.g., programmed), each of the modules need not be configured or instantiated at any one instance in time. For example, where the modules comprise a general-purpose processor configured using software, the general-purpose processor may be configured as respective different modules at different times. Software may accordingly configure a processor, for example, to constitute a particular module at one instance of time and to constitute a different module at a different instance of time.

Modules can provide information to, and receive information from, other modules. Accordingly, the described modules may be regarded as being communicatively coupled. Where multiple such modules exist contemporaneously, communications may be achieved through signal transmission (e.g., over appropriate circuits and buses) that connect the modules. In embodiments in which multiple modules are configured or instantiated at different times, communications between such modules may be achieved, for example, through the storage and retrieval of information in memory structures to which the multiple modules have access. For example, one module may perform an operation and store the output of that operation in a memory device to which it is communicatively coupled. A further module may then, at a later time, access the memory device to retrieve and process the stored output. Modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the one or more processors or processor-implemented modules may be located in a single geographic location (e.g., at a location of a mobile computing device or at a server farm). In other example embodiments, the one or more processors or processor-implemented modules may be distributed across a number of geographic locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information. Such memories may be or may include non-transitory, tangible computer-readable media configured to store computer-readable instructions that may be executed by one or more processors of one or more computer systems.

As used herein any reference to "one embodiment," "an embodiment," or "some embodiments" means that a particular element, feature, structure, or characteristic described in connection with the embodiment is included in at least one embodiment. The appearances of the phrases "in one embodiment," "in an embodiment," "in some embodiments," or similar phrases in various places in the specification are not necessarily all referring to the same embodiment or the same set of embodiments.

Some embodiments may be described using the terms "coupled," "connected," "communicatively connected," or "communicatively coupled," along with their derivatives. These terms may refer to a direct physical connection or to an indirect (physical or communicative) connection. For example, some embodiments may be described using the term "coupled" to indicate that two or more elements are in direct physical or electrical contact. The term "coupled," however, may also mean that two or more elements are not in direct contact with each other, but yet still co-operate or interact with each other. Unless expressly stated or required by the context of their use, the embodiments are not limited to direct connection.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), or both A and B are true (or present).

In addition, "a" or "an" are employed to describe elements and components of the embodiments herein. This is done merely for convenience and to give a general sense of the description. This description, and the claims that follow, should be read to include one or at least one and the singular also includes the plural, unless the context clearly indicates otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

Upon reading this disclosure, those of skill in the art will appreciate still additional alternative structural and functional designs for the systems and a methods disclosed herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

Finally, the patent claims at the end of this patent application are not intended to be construed under 35 U.S.C. § 112 (f), unless traditional means-plus-function language is expressly recited, such as "means for" or "step for" language being explicitly recited in the claims. The systems and methods described herein are directed to an improvement to computer functionality, which may include improving the functioning of conventional computers in performing tasks.

What is claimed:

1. A computer-implemented method of reducing data latency in initiating medication reconciliation processes for patients after the patients are discharged from hospitals, the computer-implemented method comprising:

training, by one or more processors, a plurality of neural networks using historical data of prescription orders issued in conjunction with hospital discharges of patients and prescription orders that were not issued in conjunction with hospital discharges of patients to discover one or more prescription attributes and/or one or more prescription attribute values that are more strongly correlated to hospital discharges than are other prescription attributes and/or prescription attribute values;

receiving, by the one or more processors, a prescription order that is to be filled for a particular patient;

predicting, by the one or more processors based upon receiving the prescription order, that the prescription order is associated with a hospital discharge of the particular patient, including:

obtaining patient data including information indicative of a hospital discharge of the particular patient, extracting one or more attributes and/or attribute values indicative of the hospital discharge of the particular patient from one or more of the prescription order or the patient data, based upon the extracted one or more attributes and/or attribute values, obtaining a trained neural network from the plurality of trained neural networks, each of the plurality of trained neural networks trained using a respective set of attributes and/or attribute values, the trained neural network trained using the respective set of attributes and/or attribute values most correlated to the extracted one or more attributes and/or attribute values, providing the extracted one or more attributes and/or attribute values as input to the trained neural network, obtaining, from a corresponding output of the trained neural network, an indication of a likelihood that the received prescription order is correlated to the hospital discharge of the particular patient, and determining that the likelihood exceeds a threshold; and responsive to determining that the likelihood exceeds a threshold, generating, by the one or more processors at a user device of one or more of healthcare providers of the particular patient, an alert indicating that the particular patient is eligible for medication reconciliation based on the prediction.

2. The computer-implemented method of claim 1, wherein:

the prescription order includes an indication of a medication; and predicting that the prescription order is associated with the hospital discharge of the particular patient includes including an indication of the medication in the input provided to the trained neural network.

3. The computer-implemented method of claim 1, wherein:

the prescription order includes an identification of a prescriber of the prescription order; and predicting that the prescription order is associated with the hospital discharge of the particular patient includes including an indication of the prescriber in the input provided to the trained neural network.

4. The computer-implemented method of claim 1, further comprising:

storing, by the one or more processors, the trained neural network on one or more memories.

5. The computer-implemented method of claim 4, wherein:

the trained neural network is generated based on performing one or more statistical analyses on the historical data of prescription orders in conjunction with one or more sets of historical data of a plurality of patients, at least some of which had been discharged from hospitals;

the computer-implemented method further comprises obtaining historical data of the particular patient; and predicting that the prescription order is associated with the hospital discharge of the particular patient includes including the one or more attributes and/or attribute values of the prescription order and one or more attributes of the historical data of the particular patient in the input provided to the trained neural network.

6. The computer-implemented method of claim 5, wherein the one or more sets of historical data of the plurality of patients include data indicative of at least one of: patient demographics, patient prescription fill history, patient pre-existing health conditions, or patient allergies.

7. The computer-implemented method of claim 1, wherein:

the one or more attributes and/or attribute values of the prescription order that are provided as the input to the trained neural network are included in one or more prescription attributes and/or one or more prescription attribute values that are more strongly correlated to hospital discharges; and the one or more attributes and/or attribute values of the prescription order that are included in the input provided to the trained neural network are indicative of one or more of: a medication, a regimen of the medication, a group of medications, a prescriber, or a location of the prescriber.

8. The computer-implemented method of claim 1, wherein generating the alert indicating that the particular patient is eligible for medication reconciliation comprises generating the alert (i) at a user interface of a computing system of a pharmacy enterprise, and/or (ii) at a user interface of a personal computing device of the particular patient or of an agent of the particular patient.

9. The computer-implemented method of claim 1, further comprising transmitting, based on the prediction that prescription order is associated with the hospital discharge of the particular patient, a request for information associated with the particular patient to at least one of: a health plan provider of the particular patient, or a medication therapy management provider.

10. The computer-implemented method of claim 9, further comprising receiving a response to the request for information associated with the particular patient, and completing a medication reconciliation process for the particular patient based on the response.

11. A system for reducing data latency in initiating medication reconciliation processes for patients after the patients are discharged from hospitals, the system associated with a pharmacy enterprise, and the system comprising:

one or more processors;

a communication interface;

one or more memories; and computer-executable instructions that are stored on the one or more memories and that, when executed by the one or more processors, cause the system to:

train a plurality of neural networks by using historical data of prescription orders issued in conjunction with hospital discharges of patients and prescription orders that were not issued in conjunction with hospital discharges of patients to discover one or more prescription attributes and/or one or more prescription attribute values that are more strongly correlated to hospital discharges than are other prescription attributes and/or prescription attribute values;

receive a prescription order that is to be filled for a particular patient;

predict based upon receiving the prescription order, that the prescription order is associated with a hospital discharge of the particular patient by:

obtaining patient data including information indicative of a hospital discharge of the particular patient, extracting one or more attributes and/or attribute values indicative of the hospital discharge of the particular patient from one or more of the prescription order or the patient data, based upon the extracted one or more attributes and/or attribute values, obtaining a trained neural network from the plurality of trained neural networks, each of the plurality of trained neural networks trained using a respective set of attributes and/or attribute values, the trained neural network trained using the respective set of attributes and/or attribute values most correlated to the extracted one or more attributes and/or attribute values, providing the extracted one or more attributes and/or one or more attribute values of the prescription order as input to a trained neural network, obtaining, from a corresponding output of the trained neural network, an indication of a likelihood that the received prescription order is correlated to the hospital discharge of the particular patient, and determining that the likelihood exceeds a threshold; and responsive to determining that the likelihood exceeds a threshold, generate, at a user device of one or more of healthcare providers of the particular patient based on the prediction, an alert indicating that the particular patient is eligible for medication reconciliation.

12. The system of claim 11, wherein:

the prescription order includes an identification of a medication; and the input to the trained neural network includes an indication of the medication.

13. The system of claim 11, wherein:

the prescription order includes an identification of a prescriber of the prescription order; and the input to the trained neural network includes an indication of at least one of the prescriber or a location of the prescriber.

14. The system of claim 11, wherein the computer-executable instructions are further executable to cause the system to:

store the trained neural network in the one or more memories.

15. The system of claim 14, wherein:

the trained neural network is generated based on performing one or more statistical analyses on one or more sets of historical prescription data in conjunction with one or more sets of historical data of a plurality of patients, some of which had been discharged from hospitals;

the computer-executable instructions are further executable to cause the system to obtain historical data of the particular patient; and the input to the trained neural network further includes one or more attributes of the historical data of the particular patient.

16. The system of claim 15, wherein the one or more sets of historical data of the plurality of patients include data indicative of at least one of: patient demographics, patient prescription fill history, patient pre-existing health conditions, or patient allergies.

17. The system of claim 11, wherein:

the one or more attributes and/or the one or more attribute values of the prescription order provided as the input to the trained neural network are included in one or more prescription attributes and/or prescription attribute values that are more strongly correlated to hospital discharges; and the one or more attributes and/or attribute values of the prescription order that are included in the input to the trained neural network are indicative of one or more of: a medication, a regimen of the medication, a group of medications, a prescriber, or a location of the prescriber.

18. The system of claim 11, further comprising a user interface, and wherein the alert is generated at (i) the user interface of the system, and/or (ii) at a user interface of a personal computing device of the particular patient or of an agent of the particular patient.

19. The system of claim 11, wherein the computer-executable instructions are further executable to cause the system to transmit, via the communication interface to a medication therapy management provider, a request for information associated with the particular patient based on the prediction that the particular patient is eligible for medication reconciliation.

20. The system of claim 19, wherein the computer-executable instructions are further executable to cause the system to complete a medication reconciliation process for the particular patient based on a response to the request for information associated with the particular patient.

* * * * *